United States Patent
Griswold et al.

(10) Patent No.: US 9,640,070 B2
(45) Date of Patent: May 2, 2017

(54) MAGNETIC RESONANCE IMAGING (MRI) WITH SELF-NAVIGATION AND SELF-REGISTRATION

(71) Applicant: Case Western Reserve University, Cleveland, OH (US)

(72) Inventors: Mark Griswold, Shaker Heights, OH (US); Vikas Gulani, Cleveland Heights, OH (US); Greg Lee, Shaker Heights, OH (US); Nicole Seiberlich, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 580 days.

(21) Appl. No.: 14/177,244

(22) Filed: Feb. 11, 2014

(65) Prior Publication Data

US 2014/0296702 A1    Oct. 2, 2014

Related U.S. Application Data

(60) Provisional application No. 61/806,907, filed on Mar. 31, 2013.

(51) Int. Cl.
*A61B 5/05* (2006.01)
*G08C 23/06* (2006.01)
(Continued)

(52) U.S. Cl.
CPC ............ *G08C 23/06* (2013.01); *A61B 5/0017* (2013.01); *A61B 5/0073* (2013.01); *A61B 5/4244* (2013.01); *A61K 49/06* (2013.01); *G01R 33/3614* (2013.01); *G01R 33/3692* (2013.01); *G01R 33/4822* (2013.01); *G01R 33/56* (2013.01); *G01R 33/5608* (2013.01);
(Continued)

(58) Field of Classification Search
CPC ....................................................... A61B 5/05
See application file for complete search history.

(56) References Cited

U.S. PATENT DOCUMENTS

| 8,761,478 | B2 * | 6/2014 | Hsieh | ............... A61B 6/032 378/4 |
| 2010/0113887 | A1 * | 5/2010 | Kalafut | ............ A61M 5/007 600/300 |

(Continued)

*Primary Examiner* — Rochelle Turchen
(74) *Attorney, Agent, or Firm* — Quarles & Brady LLP

(57) ABSTRACT

Three-dimensional (3D) projections of nuclear magnetic resonance (NMR) signals are acquired from a liver experiencing NMR in response to a 3D multi-echo non-Cartesian pulse sequence. The projections are reconstructed into two sets of images having different resolutions. Bins associated with the different positions to which the liver moves during respiration are identified in lower resolution images, and then higher resolution images are binned into the position dependent bins based on navigator data in the lower resolution images. A combined image for a bin is made from images located in the bin and then registered to a reference image. An overall combined image is made by summing the combined bin images. Quantized data for a contrast agent concentration in the liver is produced using signal intensity in the overall combined image. The quantized value may describe a liver perfusion parameter. A diagnosis may be made from the quantized value.

19 Claims, 14 Drawing Sheets

(51) Int. Cl.
*G01R 33/36* (2006.01)
*G01R 33/56* (2006.01)
*G01R 33/48* (2006.01)
*G01R 33/58* (2006.01)
*A61K 49/06* (2006.01)
*A61B 5/00* (2006.01)
*G01R 33/563* (2006.01)
*A61B 5/055* (2006.01)

(52) U.S. Cl.
CPC ....... *G01R 33/56366* (2013.01); *G01R 33/58* (2013.01); *A61B 5/055* (2013.01)

(56) References Cited

U.S. PATENT DOCUMENTS

| | | | |
|---|---|---|---|
| 2011/0044524 A1* | 2/2011 | Wang | G01R 33/54 382/131 |
| 2015/0006114 A1* | 1/2015 | Altbach | G01R 33/50 702/189 |

\* cited by examiner

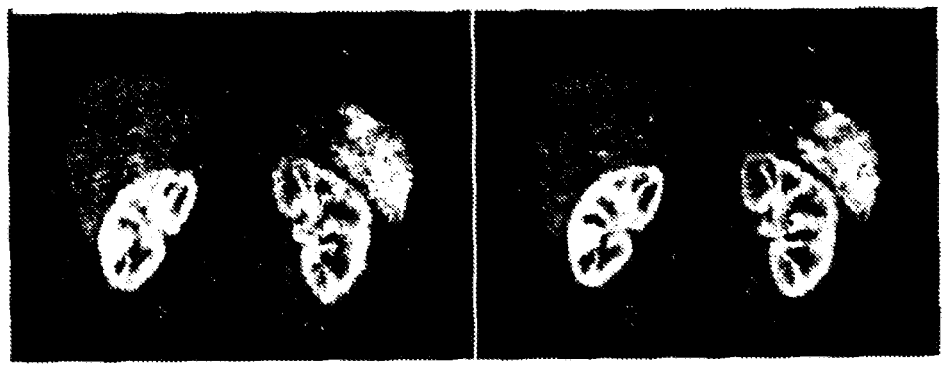
Figure 10A                    Figure 10B

MAGNETIC RESONANCE IMAGING (MRI) WITH SELF-NAVIGATION AND SELF-REGISTRATION

CROSS REFERENCE TO RELATED APPLICATIONS

This application claims the benefit of U.S. Provisional Patent Application 61/806,907 titled "Medical Imaging" filed Mar. 31, 2013.

FEDERAL FUNDING NOTICE

The invention was developed with federal funding supplied under Federal Grant Nos. R01 HL094557, R00EB011527, and 2KL2RR00040 provided by the National Institute of Health (NIH). The Federal government has certain rights in the invention.

BACKGROUND

Magnetic resonance imaging (MRI) provides highly detailed anatomical information. Dynamic contrast-enhanced (DCE) MRI of the liver monitors the arrival, transit, or presence of contrast materials (e.g., gadolinium (Gd) chelates) through the liver. DCE MRI of other portions of the body (e.g., kidney, lung) may also monitor the arrival, transit, or presence of contrast materials. Conventionally, acquiring DCE abdominal images has been challenging due, for example, to motion artifacts caused by patient movement during multiple breath holds. It may be difficult to accommodate requests for multiple lengthy breath holds while a patient with a potentially compromised organ is in the bore while a contrast agent is being applied.

Acquiring useful images of the liver has been challenging due to the combination of a large volume to be covered, desired high spatial resolution, and rapidly changing contrast conditions in the post-contrast images. All of these factors are complicated by the need for multiple lengthy breath holds by a patient with a possibly compromised liver. Typical post contrast sequences may have required 15-20 second breath holds carefully coordinated with contrast agent administration, arrival, and uptake, which effectively precluded time-course analysis and which frequently resulted in motion-corrupted exams upon breath-hold failure.

Different contrast agents have been employed in liver MRI. For example, Gd-DTPA was used as early as 1988. More recently, Gd-BOPTA (gadolinium benzyloxy-propionic tetraacetate or gadobenate dimeglumine) and Gd-EOB-DTPA (gadolinium ethozybenzyl diethylenetriamine-pentaacetic acid) have been used. Gadolinium based contrast agents are typically employed to shorten T1 in regions where the Gd concentrates. Gd-BOPTA is distributed in the body like ordinary extracellular contrast agents (e.g., Gd-DTPA). However, in the liver, Gd-BOPTA is taken up by hepatocytes and is excreted into the biliary canaliculi in an adenosine triphosphate (ATP) dependent process. Hepatocytes are polarized cells that have two functionally distinct sides, including one that faces the blood and extracellular fluids. Gd-BOPTA enhancement may reach a peak 60-120 minutes after contrast agent introduction. Gd-EOB-DTPA combines hepatocellular specificity with T1-relaxivity and extracellular behavior. Gd-EOB-DTPA is first distributed into the extracellular spaces and then taken up by hepatocytes. Gd-EOB-DTPA enhancement may reach a peak in the liver about 20 minutes after contrast agent introduction.

Conventional approaches have typically employed T1-weighted, gradient recalled echo (GRE) sequences. T1 refers to spin-lattice relaxation, T2 refers to spin-spin relaxation. T1 relaxation is caused by interactions between excited protons and local electromagnetic fields associated with neighboring structures. T2 relaxation depends on the continuous de-phasing of precessing protons caused by local magnetic field inhomogeneities. T2 is faster than T1. A GRE sequence applies varying gradient fields to refocus spins. A spin echo (SE) sequence uses RF pulses to refocus spins. An echo planar imaging (EPI) sequence may be used to acquire all the spatial-encoding data of an image after a single radio-frequency (RF) excitation. Instead of measuring just one echo after an excitation pulse, EPI acquires many echoes. Echoes may be acquired as long as the precessing magnetization in the xy plane has not decayed beyond an acquisition threshold. EPI may be thought of as an "add-on" to a pulse sequence that facilitates acquiring more signals from each excitation pulse. When an EPI acquisition strategy is used, all k-space lines may be measured in one TR of a gradient echo sequence or a spin echo sequence.

Three-dimensional (3D) acquisitions may have provided continuous whole-liver coverage to assess whole-liver perfusion, but have been limited by longer acquisition times. 3D T1 mapping within one breath-hold has typically been challenging given the size of the liver. Thus, two-dimensional (2D) images have typically been acquired with higher temporal and spatial resolution. However, the 2D image approach may have been limited to a single representative slice or selected slices, which precluded whole liver perfusion analysis. Achieving higher temporal and spatial resolution facilitates achieving greater precision in estimating liver perfusion rates.

In 2012, a rotating 2D multi-echo approach was described in Lee et al., Proc. ISMRM 2012, p. 3012. This approach produced relatively equidistant samples regardless of time scale. This approach was applied in time-resolved four dimensional (4D) contrast-enhanced MR angiography. See, for example, Rapid Time-Resolved Magnetic Resonance Angiography via a Multiecho Radial Trajectory and GraDes Reconstruction, Lee et al., MRM 2012 (doi: 10.1002/mrm.24256). This approach may be referred to herein as the Lee approach. In the angiography application, performing reconstruction at a long time scale (e.g., around 2 minutes) allowed sensitivity maps and field maps to be computed. Performing reconstruction at a shorter time scale (e.g., around 1-2 seconds) allowed dynamic imaging of the vasculature.

The 3D multi-echo non-Cartesian echo planar imaging (EPI) Lee approach employs pseudo-random rotations of a single 2D multi-echo non-Cartesian readout in a multi-shot trajectory. The trajectory produces incoherent aliasing artifacts and a relatively uniform distribution of projections over different time scales. A field map is computed from the same data set and is used to avoid signal dropout in regions of substantial field inhomogeneity. A compressed sensing reconstruction using a gradient descent with sparsification (GraDeS) algorithm may be employed. The GraDeS algorithm as adapted for use with multi-coil MRI data is given by:

$$\hat{x}_n = \hat{x}_{n-1} + \frac{1}{\gamma} \sum_{i=1}^{n_c} C_i^* F^* D(y_i - FC_i \hat{x}_{n-1})$$

where $\hat{x}_n$ is the image estimate after iteration number n, $C^*_i$ are the complex conjugate coil sensitivities, and $F^*$ is the adjoint NUFFT operation (non-Cartesian k space to image space). The summation corresponds to a multi-coil gridding reconstruction of the difference between the acquired k space data, y, and k space values corresponding to the current image estimate. The new estimate is made by moving a step size $1/\gamma$ along this gradient. The procedure progressively reduces the error $\|y-Ax\|^2$.

In the GraDeS algorithm, using a larger number of iterations improves temporal behavior at the cost of decreased image signal-to-noise ratio (SNR). The GraDeS algorithm assumes that at a point in time, the difference between a current frame and a previous frame should be minimal. However, in objects that experience significant movement due, for example, to respiration, the frames may differ by an unacceptable amount. Conventionally this may have limited the Lee approach to imaging static objects.

In the Lee angiography approach, when using a multi-channel receiver array for data acquisition, the resulting k space data is made up of $n_c$ sets corresponding to each of the individual coils. $y_i$ is the k space data corresponding to coil i. and x corresponds to the object to be reconstructed. The relationship between image space and k space is given by:

$$y = A_x \text{ where } y = \begin{bmatrix} y_1 \\ \vdots \\ y_{n_e} \end{bmatrix} A = \begin{bmatrix} FC_1 \\ \vdots \\ FC_{n_e} \end{bmatrix}$$

The matrix A is a system matrix representing the linear transformation of an image to multi-coil k space data. $C_i$ are diagonal matrices containing the complex coil sensitivities, and F is a matrix representing a linear transformation from image space to k space. In the non-Cartesian (e.g., radial) case, F may represent a Fourier transform followed by interpolation from a Cartesian k space grid to the non-Cartesian k space locations, which may be referred to as a non-uniform fast Fourier transform (NUFFT). A gridding reconstruction for multi-coil data is described by:

$$\hat{x}_{grid} = \Sigma_{i=1}^{n_e} C^*_i F^* D_{y_i}$$

where D is a diagonal matrix containing the density compensation weights for each k space sample. Density compensation accounts for the non-uniform sampling density present in the radial k space sampling pattern. $C^*_i$ are the complex conjugate coil sensitivities, and $F^*$ is the adjoint NUFFT operation.

The Lee angiography method involves sampling a number of radial lines within a single plane using a 2D radial echo-planar imaging (EPI) trajectory. Multiple rotations of the same 2D trajectory are used to fill in 3D k space. A pseudo-random schedule of rotations is employed to produce incoherent aliasing artifacts at any arbitrarily chosen number of shots per reconstructed image frame. The full set of shots may be used to determine coil sensitivity maps. The individual echoes of the multi-echo radial trajectory are used to determine a field map.

In one example of the Lee approach, images were acquired using a non-Cartesian 3D FLASH acquisition (TR=8.68 ms, flip angle=20, 1-mm isotropic resolution), with a 3T scanner. A minimum-phase radiofrequency pulse (duration 600 µs, tip-down time 140 µs from end) was used for slab-selective excitation. A 2D radial EPI trajectory having five projections per shot (duration=6.44 ms) was acquired in each TR interval starting at echo time=0.26 ms. The additional echo time (TE) times within the readout for the full echoes were 1.63, 2.89, 4.15, and 5.42 ms. Data were acquired continuously throughout the trajectory duration. A 2.6-µs sampling interval (2476 total samples) was used, corresponding to 2-fold oversampling along each readout line. Pseudo-random rotations of the 2D pattern were used to progressively fill in 3D k space over multiple shots.

Thus, the Lee angiography approach involved acquiring data using a 3D multi-echo non-Cartesian (e.g., radial) approach by using pseudo-random rotations of a single 2D multi-echo non-Cartesian readout, and then reconstructing the acquired data using a compressed sensing reconstruction with GraDeS. The approach may have been susceptible to motion artifacts in a moving object.

BRIEF DESCRIPTION OF THE FIGURES

FIG. 10A illustrates an image reconstructed without registration of the temporal volumes.

FIG. 10B illustrates the same image as FIG. 10A reconstructed with registration of the temporal volumes.

DETAILED DESCRIPTION

Example apparatus and methods employ a multi-echo 3D non-Cartesian (e.g., radial) acquisition that produces relatively equidistant samples regardless of timescale. Example apparatus and methods correct for respiratory motion in the multi-echo 3D non-Cartesian acquisition using image-domain based self-navigation and sub-volume registration. The respiratory motion is non-rigid and thus may not be compensated for using simple corrections to raw k-space data. Instead, a more sophisticated pencil-beam navigator based binning approach combined with non-linear sub-volume registration may be employed. The multi-resolution sampling properties of the 3D radial acquisition facilitate image-domain self-navigation and sub-volume registration of free-breathing abdominal issues, which may mitigate motion corruption of abdominal MR exams.

The primary component of respiration-related liver motion is in the superior/inferior direction. The superior surface of the liver comprises a part of both lobes. The superior surface is, as a whole, convex. The superior surface fits under the vault of the diaphragm, which in front separates it on the right from the sixth to the tenth ribs and their cartilages, and on the left from the seventh and eighth costal cartilages. The middle part of the superior surface lies behind the xiphoid process. The middle part of the superior surface is in contact with the abdominal wall in the angle between the diverging rib cartilage of opposite sides. The inferior surface of the liver is uneven, concave, directed downward, backward, and to the left. The inferior surface of the liver is almost completely invested by peritoneum. The inferior surface of the left lobe presents behind and to the left the gastric impression. As a person breathes, the liver changes shape and moves in the superior/inferior direction and also changes shape and moves in the anterior to posterior direction.

Figure 12A:
FIG. 12A illustrates an extracted pencil beam navigator time course.
Figure 12B:
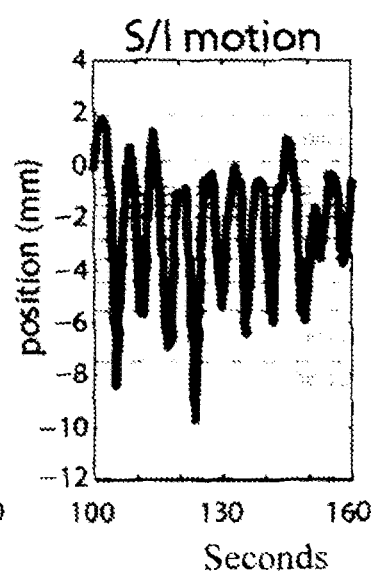
FIG. 12B illustrates a motion estimate corresponding to the pencil beam navigator time course illustrated in FIG. 12A.
Figure 13:
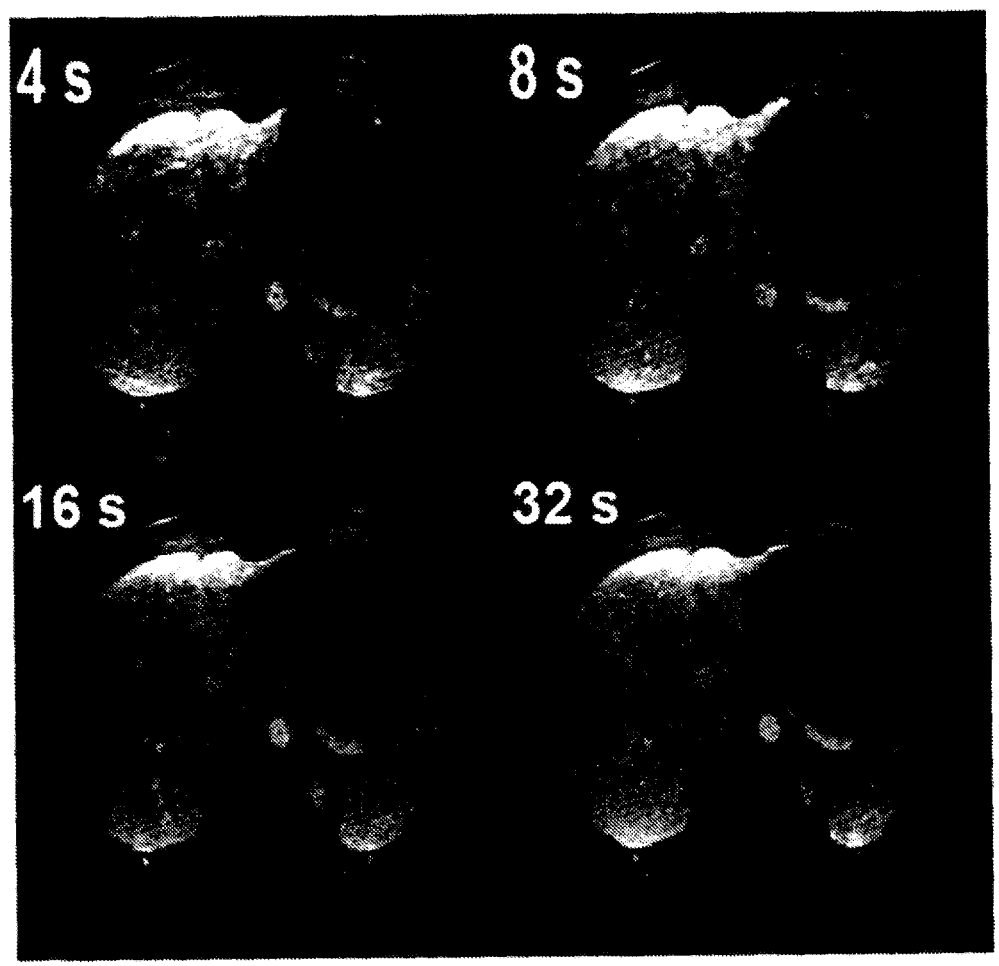
FIG. 13 illustrates images reconstructed at 4, 8, 16, or 32 second temporal footprints. The images were taken 50 seconds post-injection of a contrast agent.

Example methods and apparatus use a multi-echo approach to acquire 3D projections using a series of 2D multi-echo non-Cartesian readouts that rotate a sampling pattern. The 3D projections may be re-ordered to be substantially equidistant in different time scales. The 3D projections may be reconstructed twice: once into high-resolution images that will be used to produce images that can be analyzed for quantitative data or that can be displayed, and once into low-resolution images that will be used for self-navigation. Navigator voxels are identified in the low-resolution images and then used to understand how the liver is moving. A pencil beam navigator time course is illustrated in FIG. 12A. FIG. 12B illustrates a motion estimate corresponding to the pencil beam navigator time course illustrated in FIG. 12A.

Figures 11A, 11B, 11C, 11D, 11E, 11F, 11G:
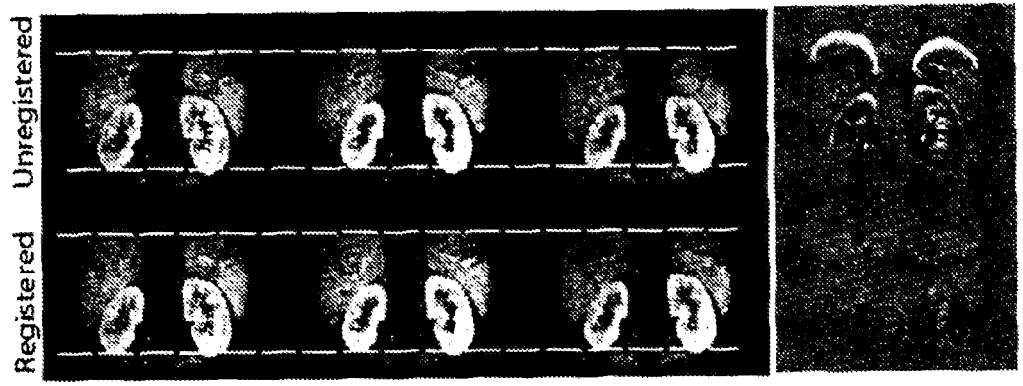
FIG. 11A illustrates an image formed using multiple projections in a bin without registering to correct for motion.
FIG. 11B illustrates an image formed using multiple projections in a bin with registering to correct for motion.
FIG. 11C illustrates an image formed using multiple projections in a bin without registering to correct for motion.
FIG. 11D illustrates an image formed using multiple projections in a bin with registering to correct for motion.
FIG. 11E illustrates an image formed using multiple projections in a bin without registering to correct for motion.
FIG. 11F illustrates an image formed using multiple projections in a bin with registering to correct for motion.
FIG. 11G illustrates residual intensity differences at the level of the noise in the subtraction of the registered images.

A set of bins corresponding to different positions of the liver are produced using a time course that is extracted from the navigator data. The high-resolution images are "binned" into the bins as a function of the navigator voxels in corresponding low-resolution images. A "per-bin" image can be made for a bin from high-resolution images that were binned into the bin. "Per-bin" images can be registered to a reference image to facilitate combining per-bin images from multiple bins into a final combined image. FIG. 10A illustrates an image reconstructed without registration of the temporal volumes while FIG. 10B illustrates the same image as FIG. 10A reconstructed with registration of the temporal volumes. FIGS. 11A, 11C, and 11E illustrate images formed using multiple projections in a bin without registering to correct for motion while FIGS. 11B, 11D, and 11F illustrate an image formed using multiple projections in a bin with registering to correct for motion.

The final combined image can be displayed or can be analyzed to produce quantitative data. In one embodiment, a diagnosis may be made from the quantitative data. A series of final combined images can be used to produce a four-dimensional (4D) "through-time" image. Concentration time courses can be identified in the 4D image and quantitative data about the concentration time courses can be produced. In one embodiment, a diagnosis may be made from the quantized data.

Figures 14A, 14B, 14C, 14D:
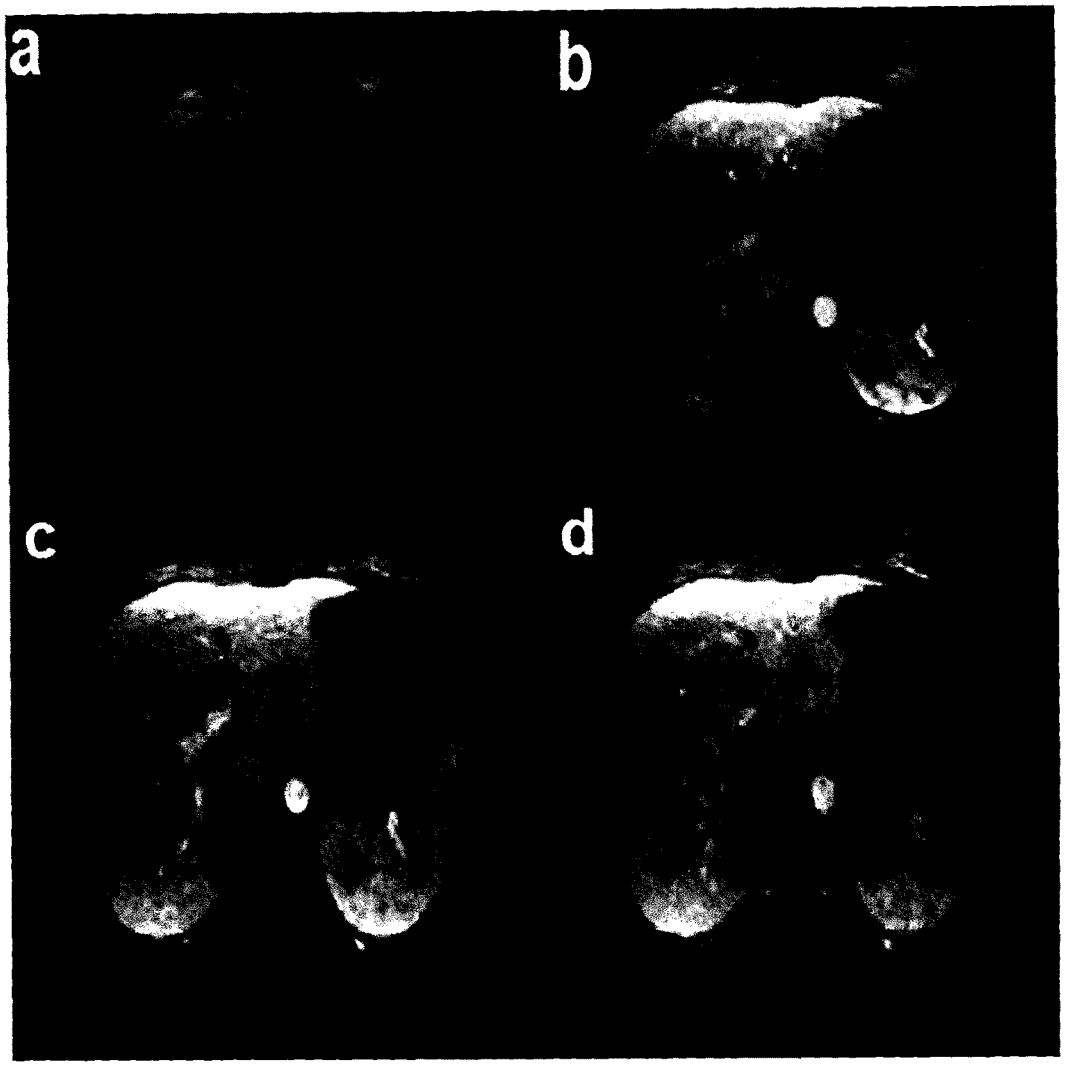
FIG. 14A illustrates an image before contrast agent uptake.
FIGS. 14B, 14C, and 14D illustrate images reconstructed at 16 second intervals during contrast agent uptake.

The quantized data support analyzing liver parameters including perfusion. Example apparatus and methods perform quantitative dynamic contrast enhanced (DCE) MRI using non-Cartesian parallel imaging techniques. Example apparatus may use values quantified from MRI data to examine liver parameters including, for example, total hepatic perfusion, arterial fraction, arterial perfusion, portal venous perfusion, vascular transit time, fractional vascular volume, or fractional extravascular extracellular volume. A series of related images may be acquired over time to support four dimensional (4D) (e.g., functional, through-time) analyses. For example, FIG. 14A illustrates a liver before contrast agent uptake and FIGS. 14B, 14C, and 14D show the liver at different times during contrast agent uptake.

In one embodiment, values quantified from MRI data may be used to make a diagnosis or to mark a series of images as being suitable for additional study. For example, quantified values associated with liver perfusion may be used to identify whether cirrhosis is present. In one embodiment, when quantified values show liver perfusion above 65 ml/min/100 ml then a preliminary diagnosis of no cirrhosis may be made. Similarly, when quantified values show liver perfusion below 35 ml/min/100 ml then a preliminary diagnosis of cirrhosis may be made. In one embodiment, when quantified values show portal perfusion above 55 ml/min/100 ml then a preliminary diagnosis of no cirrhosis may be made while quantified values showing portal perfusion below 15 ml/min/100 ml may lead to a preliminary diagnosis of cirrhosis. In one embodiment, when quantified values show arterial perfusion below 8 ml/min/100 ml then a preliminary diagnosis of no cirrhosis may be made while quantified values showing arterial perfusion above 20 ml/min/100 ml may lead to a preliminary diagnosis of cirrhosis. In one embodiment, when quantified portal fraction volume is above 80% then a preliminary diagnosis of no cirrhosis may be made while a quantified portal fraction volume below 40% may lead to a diagnosis of cirrhosis. In one embodiment, when quantified mean transit time is below 12 seconds then a preliminary diagnosis of no cirrhosis may be made while quantified mean transit time above 30 seconds may lead to a preliminary diagnosis of cirrhosis. Different values for different diagnoses may be used in different embodiments.

Experiments that included free-breathing liver DCE MRI were performed on asymptomatic volunteers following injection of Gd-DTPA on a 3T MRI apparatus. Gd refers to gadolinium. In one embodiment, a multi-echo 3D radial FLASH pulse sequence was employed. In one example, an MRI readout was employed with repetition time (TR) set to 8.4 ms. Other TRs may be employed. In one example, a field of view (FOV) was set to 380 mm with 9 radial lines per shot which yielded effective resolution of 1.8 mm isotropic. Other FOV and numbers of radial lines may be employed. Resolution of 1.9 mm in-plane is sufficient to support high precision functional examinations that provide quantitative data about liver perfusion.

Acquiring the data is just part of the procedure for producing quantized data concerning liver perfusion. The magnetic resonance (MR) signal data may be quantized by converting signal intensity in the MR signal data to contrast agent concentration. In one example, to quantize results, signal intensity values may be converted to contrast agent concentration based, at least in part, on reference or calibration values provided from imaging of reference samples. The reference samples may be, for example, vials with known concentrations of the contrast agent. With quantized concentration values available, concentration time courses may be produced and then employed to estimate or illustrate perfusion parameters. The parameters may be estimated using, for example, a non-linear least squares fit approach. The quantized concentration values may be produced or analyzed based, at least in part, on a compartment model of the liver.

In one example, a dual input single compartment model may be used to obtain estimates of perfusion parameters based, at least in part, on the quantized contrast agent concentration. The studied parameters may include total hepatic perfusion, arterial fraction, distribution time, mean transit time, arterial perfusion, portal venous perfusion, vascular transit time, fractional vascular volume, or fractional extravascular extracellular volume. Other parameters may also be examined. While a dual input single compartment model is described, in other examples different compartment models may be employed.

In different embodiments, signal intensity may be measured in the aorta, in the portal vein, or in the liver parenchyma. The measured signal intensity may then be converted to Gd concentrations. Producing quantized data about contrast agent concentration facilitates producing outputs that may not be available to conventional systems.

Figure 1:
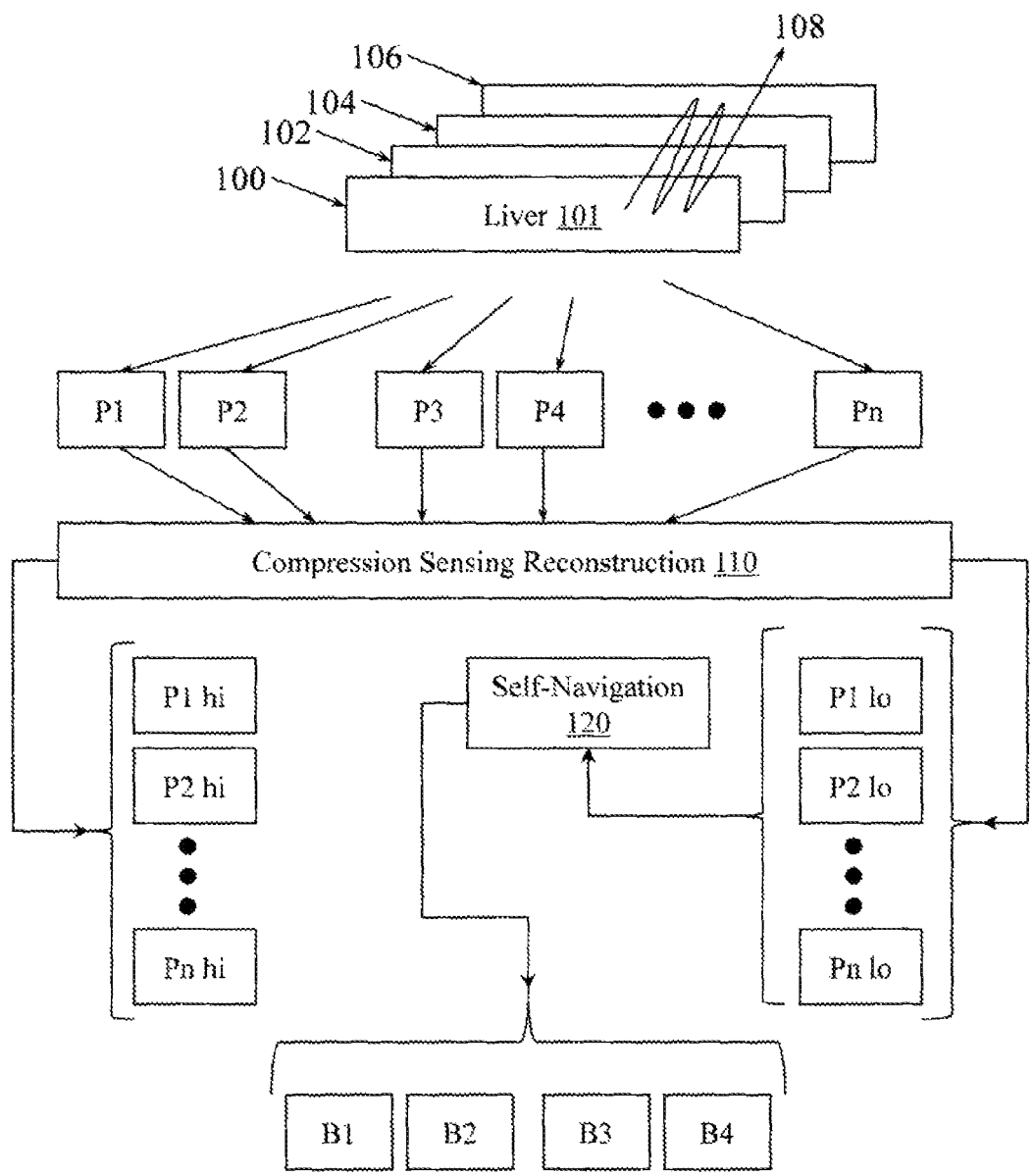
FIG. 1 illustrates a portion of a data flow associated with an MRI 3D multi-echo non-Cartesian approach with self-navigation and self-registration.

FIG. 1 illustrates a portion of a data flow associated with an MRI 3D multi-echo non-Cartesian approach with self-navigation and self-registration. A liver 101 may move in a superior/inferior direction. Repeated motion may produce a path or motion time course 108. At different repeated times the liver 101 may be at location 100, location 102, location 104, and location 106. While four locations are illustrated, a greater or lesser number of locations may be identified or used. Projections P1, P2, P3, and P4 through Pn may be acquired from the liver 101. The projections may be acquired in response to the 3D multi-echo non-Cartesian approach. The approach may resemble the Lee technique. The projections may be reconstructed using a compression sensing reconstruction 110. The projections may be reconstructed two or more different ways. For example, the projections may be reconstructed into a set of high-resolution images P1 hi, and P2 hi through Pn hi. The high-resolution may be, for example, better than 2.0 mm³ isotropic. The projections may also be reconstructed into a set of low-resolution images P1 lo, and P2 lo through Pn lo. The low-resolution may be, for example, less than 20.0 mm³. Different choices for the high resolution and low resolution may be employed. In one embodiment, projections may be reconstructed from a one second data window every half a second.

The low-resolution images may be analyzed by a self-navigation 120 that produces a set of bins that are related to the positions identified in path 108 for liver 101. FIG. 1 illustrates four bins B1, B2, B3, and B4 that correspond to locations 100, 102, 104, and 106. While four positions and four bins are used, a greater or lesser number of positions and bins may be used. While the number of bins corresponds to the number of positions, a one-to-one correspondence may not be required. A "bin" refers to a logical container with which high-resolution images may be associated or "binned". Binning an image may include, for example, storing an image in a data structure, storing a pointer to an image in a data structure, updating a database record, writing a value in a table, or other action.

Figure 2:
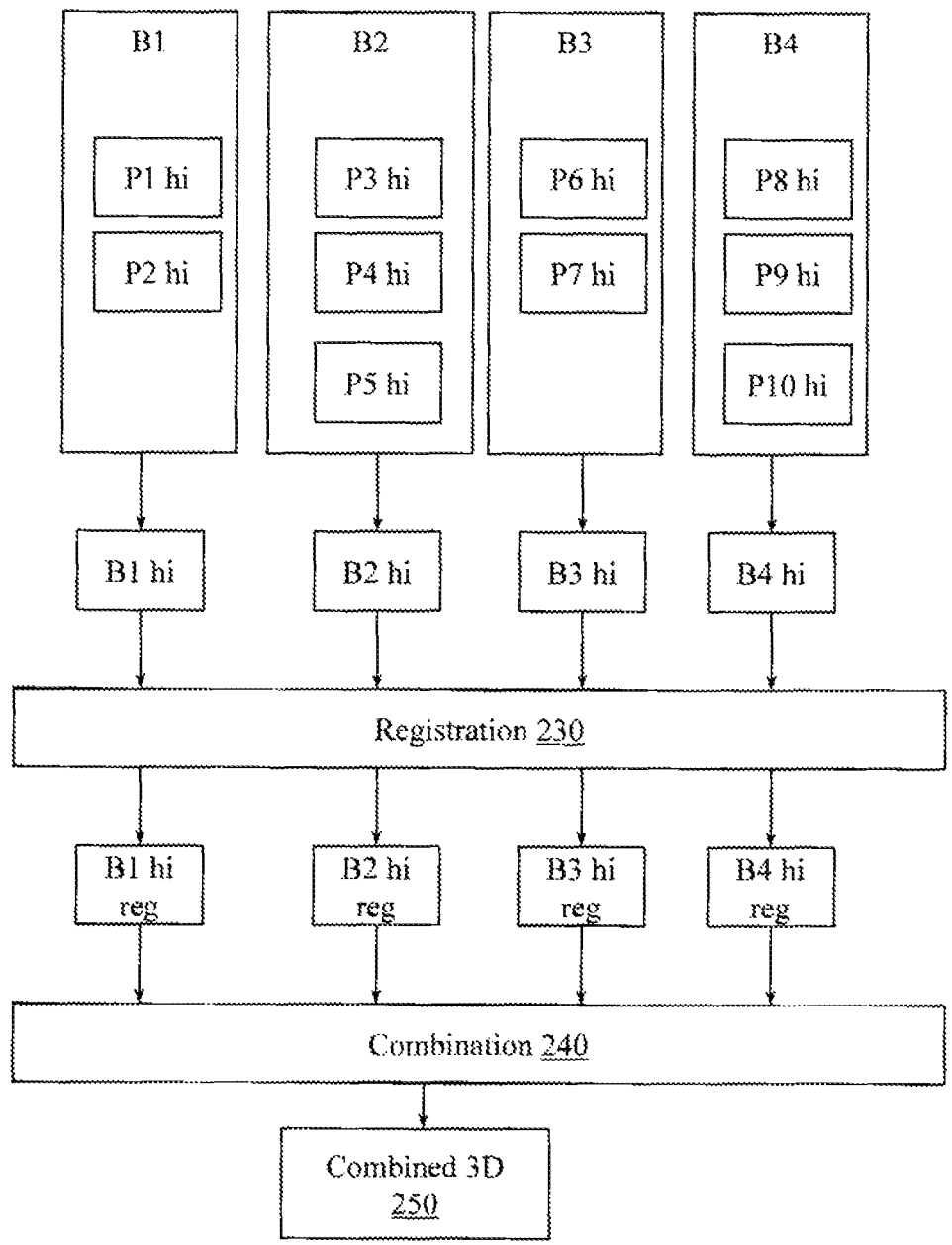
FIG. 2 illustrates a portion of a data flow associated with an MRI 3D multi-echo non-Cartesian approach with self-navigation and self-registration.

FIG. 2 illustrates a portion of a data flow associated with an MRI 3D multi-echo non-Cartesian approach with self-navigating and self-registration. The portion illustrated in FIG. 2 picks up at the bins B1, B2, B3, and B4 illustrated in FIG. 1. FIG. 2 illustrates the bins after high-resolution images have been associated with the bins. Bin B1 is illustrated having high-resolution images P1 hi and P2 hi, bin B2 is illustrated having high-resolution images P3 hi, P4 hi, and P5 hi, bin B3 is illustrated having high-resolution images P6 hi and P7 hi, and bin B4 is illustrated having high-resolution images P8 hi, P9 hi, and P10 hi. Bins may or may not have any images and may or may not have equal numbers of images.

FIG. 2 also illustrates "per bin" images being created for the bins. For example, a per bin image B1 hi is produced from p1 hi and P2 hi in bin B1. Similarly, a per bin image B2 hi is produced from P3 hi, P4 hi, and P5 hi, per bin image B3 hi is produced from the images in B3 and per bin image B4 is produced from the images in B4. The per bin images may then be registered using registration 230. Registering the per bin images may include aligning a per bin image to a reference image. For example, the image associated with bin B2 (e.g., B2 hi) may be selected as the reference image and the other per bin images B1 hi, B3 hi, and B4 hi may be registered to B2 hi. The registration may be performed using, for example, non-linear registration with FMRT from FMRIB. See, for example. Andersson et al., FMRIB Technical Report TR07JA2, 2007. Registration 230 may produce registered per bin images B1 hi reg, B2 hi reg, B3 hi reg, and B4 hi reg. The registered per bin images may then be combined through combination 240 into a combined 3D image 250. In one embodiment, the resolution for combined 3D image 250 may be selected retrospectively.

Figure 3:
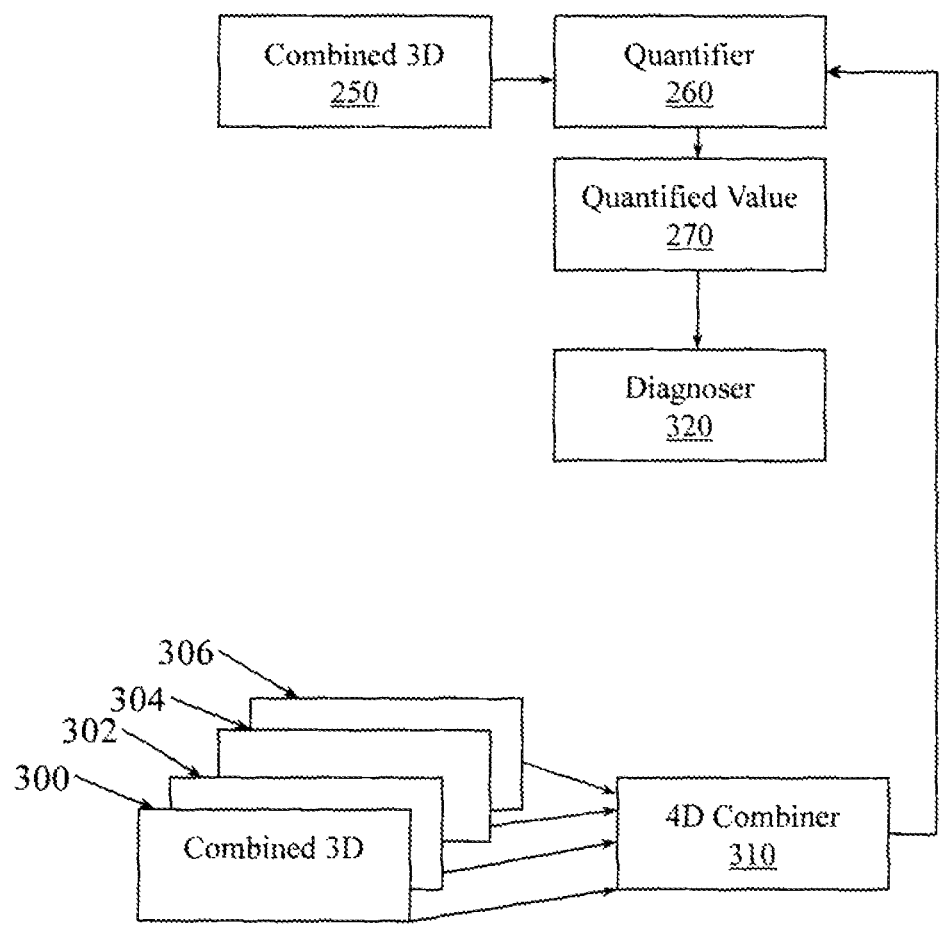
FIG. 3 illustrates a portion of a data flow associated with an MRI 3D multi-echo non-Cartesian approach with self-navigation and self-registration.

FIG. 3 illustrates a portion of a data flow associated with an MRI 3D multi-echo non-Cartesian approach with self-navigation and self-registration. FIG. 3 starts at the combined 3D image 250 described in FIG. 2. The combined 3D image 250 may be provided to a quantifier 260 that produces a quantified value 270. The quantified value 270 may be produced by analyzing signal intensities in the combined 3D image 250. In one embodiment, the signal intensities may be analyzed by comparing them to reference intensities acquired from phantoms. In one embodiment, the quantified value 270 may then be used by a diagnoser 320 to make a diagnosis. For example, a diagnosis of cirrhosis of the liver may be made based on the quantified value 270.

The data flow illustrated in FIG. 1 and FIG. 2 may be used to produce a series of combined 3D images. The series may be collected over a period of time. For example, a first combined 30 image 300 may be produced from data acquired during the first sixteen seconds of a DCE MRI procedure, another combined 3D image 302 may be produced from data acquired during the next sixteen seconds of the DCE MRI procedure, another combined 3D image 304 may be produced from data acquired during the next sixteen seconds of the DCE MRI procedure, and another combined 3D image 306 may be produced from data acquired during the next sixteen seconds. A greater or lesser number of combined 3D images may be produced or used. Members of the series of combined 3D images may be provided to a 4D combiner 310. Combiner 310 may then produce a 4D image that can also be analyzed by, for example, quantifier 260 to produce a quantified value 270 that a diagnoser 320 can use to produce a diagnosis.

Some portions of the detailed descriptions that follow are presented in terms of algorithms and symbolic representations of operations on data bits within a memory. These algorithmic descriptions and representations are used by those skilled in the art to convey the substance of their work to others. An algorithm is considered to be a sequence of operations that produce a result. The operations may include creating and manipulating physical quantities that may take the form of electronic values. Creating or manipulating a physical quantity in the form of an electronic value produces a concrete, tangible, useful, real-world result.

It has proven convenient at times, principally for reasons of common usage, to refer to these signals as bits, values, elements, symbols, characters, terms, numbers, and other terms. It should be borne in mind, however, that these and similar terms are to be associated with the appropriate physical quantities and are merely convenient labels applied to these quantities. Unless specifically stated otherwise, it is appreciated that throughout the description, terms including processing, computing, and determining, refer to actions and processes of a computer system, logic, processor, or similar electronic device that manipulates and transforms data represented as physical quantities (e.g., electronic values).

Example methods may be better appreciated with reference to flow diagrams. For simplicity, the illustrated methodologies are shown and described as a series of blocks. However, the methodologies may not be limited by the order of the blocks because, in some embodiments, the blocks may occur in different orders than shown and described. Moreover, fewer than all the illustrated blocks may be required to implement an example methodology. Blocks may be combined or separated into multiple components. Furthermore, additional or alternative methodologies can employ additional, not illustrated blocks.

Figure 4:
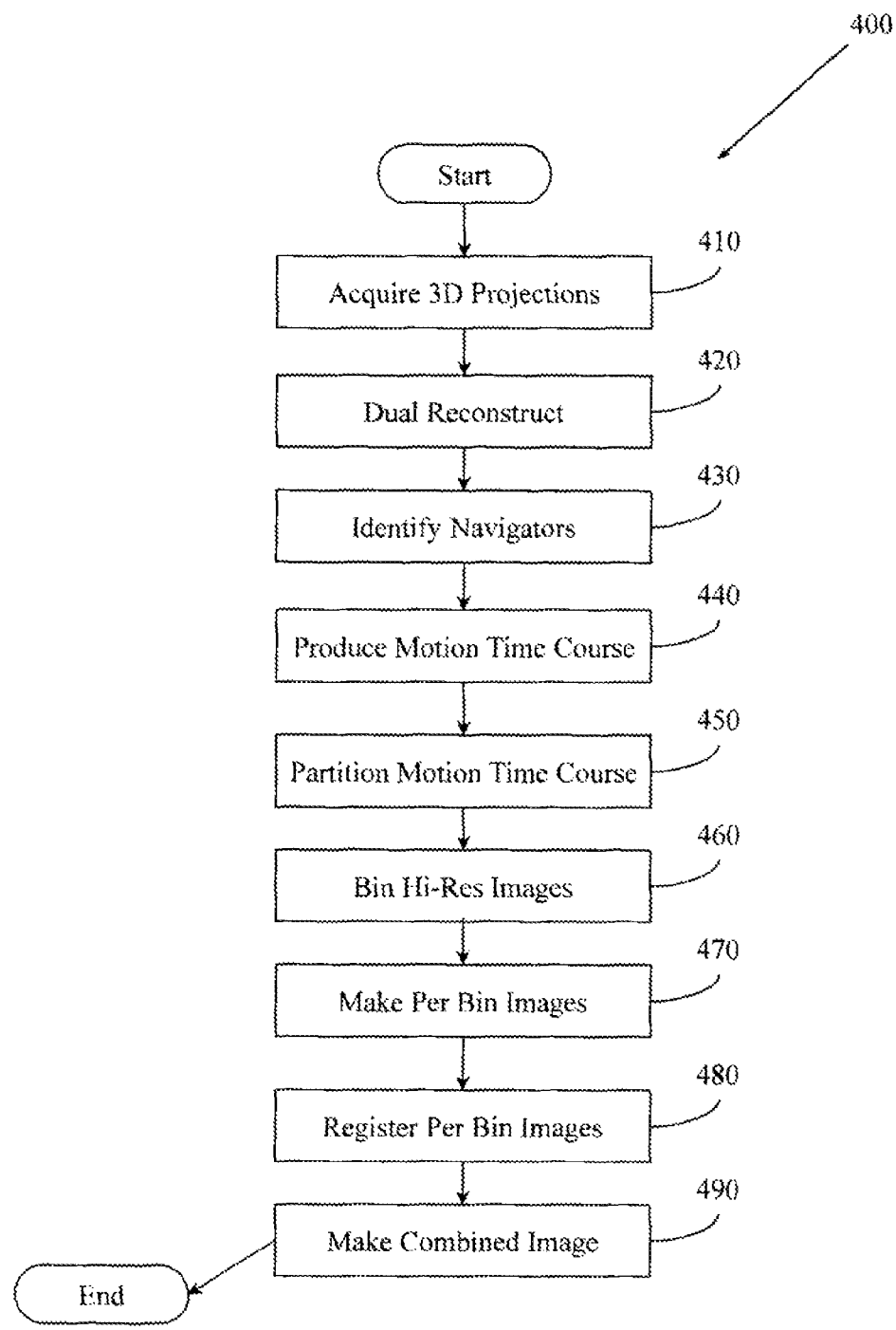
FIG. 4 illustrates an example method associated with an MRI 3D multi-echo non-Cartesian approach with self-navigation and self-registration.

FIG. 4 illustrates an example method 400 associated with high-quality quantitative MRI-DCE liver analysis. Method 400 includes, at 410, controlling an MRI apparatus to acquire a set of 3D projections. The set of 3D projections may be collected from a liver that moves due to respiration. The liver may move, for example, in a superior/inferior direction. In one embodiment, the set of 3D projections are acquired using a 3D multi-echo non-Cartesian acquisition. In one embodiment, the set of 3D projections are acquired during a DCE MRI procedure that includes presenting a contrast agent to the liver. The contrast agent may be, for example, Gd-BOPTA. The DCE MRI procedure may cause different enhancements in the liver.

In one embodiment, method 400 may include ordering the set of 3D projections so that members of the set are equidistant to within a tolerance. The tolerance may be, for example, a rotation, a distance, an angle, or other measure. In one embodiment, acquiring a member of the set of 3D projections includes performing two or more pseudo-random rotations of a single 2D multi-echo non-Cartesian readout. The two or more pseudo-random rotations may populate 3D spherical k-space by rotating a sampling pattern. In one embodiment, the 3D multi-echo non-Cartesian acquisition may be a radial echo planar imaging (EPI) acquisition. The 3D multi-echo non-Cartesian acquisition may use a fast low angle shot (FLASH) pulse sequence. In one embodiment, the approach employed in Lee may be used.

Method 400 may include creating a field map and a sensitivity map from the set of 3D projections. The field map or sensitivity map may then be used to correct for susceptibility related distortions in the set of 3D projections.

Method 400 also includes, at 420, controlling the MRI apparatus to reconstruct members of the set of 3D projections. The reconstruction may be a dual reconstruction where a first reconstruction is performed in the superior/inferior direction to produce a corresponding set of first 3D images using a compressed sensing reconstruction. In one embodiment, the compressed sensing reconstruction uses a gradient descent with sparsification (GraDeS) approach. The members of the set of first 3D images have a first resolution (e.g., 2.0 mm$^3$). Other resolutions may be employed. The dual reconstruction may also include a second reconstruction performed in plane to produce another corresponding set of second 3D images using the compressed sensing reconstruction. Members of the set of second 3D images may have a second resolution (e.g., 10 mm$^3$) that is less than the first resolution. Other resolutions may be employed. The set of first 3D images may be used to make images while set of second 3D images may be used for navigation.

Thus method 400 may include, at 430, identifying one or more in-plane navigator voxels in members of the set of second 3D images. In one embodiment, a single navigator voxel may be selected while in another embodiment a collection of related (e.g., adjacent) voxels may be employed. The navigator voxel may be located in the dome of the liver.

The navigator voxel may be tracked in the low resolution set of second 3D images as the liver moves, for example, in the superior/inferior direction. Therefore, method 400 may include, at 440, producing a plot of the signal intensity of the one or more in-plane navigator voxels. The plot may reflect the location of the navigator voxel(s) in two or more of the set of second 3D images along the path traveled by the liver as a function of time. The plot may be used to identify a motion time course for the liver. The plot may depend, at least in part, on the plot of the signal intensity associated with the navigator voxel(s).

Once the motion of the liver is understood by analyzing the plot, method 400 may continue, at 450, by partitioning the motion time course into a set of position-dependent intervals. In one embodiment, two intervals may be used. In another embodiment, four intervals may be used. Different numbers of intervals may be used in different embodiments. The intervals may be used as "bins" into which members of the high resolution first set of 3D images can be placed.

Method 400 may include, at 460, binning the high-resolution images. Placing an image into a bin may be a physical operation where bits that define an image are transferred to a data store or may be a logical operation where a pointer to an image may be manipulated. Other operations may be employed to bin an image. Binning an image may include associating a member of the set of first 3D images with a member of the set of position-dependent intervals based, at least in part, on the motion time course and the one or more in-plane navigator voxels.

Once the high-resolution images are binned, method 400 may proceed, at 470, to produce a 3D image for an interval from the set of position-dependent intervals using members of the set of first 3D images associated with the interval. The 3D image for the interval may have a third resolution that is different from either the first or second resolution. In one embodiment, a "per bin" image is made for each of the bins using all of the high-resolution images that were binned into that bin. In other embodiments, less than all the high-resolution images for a bin may be employed and less than all bins may be processed. For example, a bin that has more than a threshold number (e.g., 4) of images may be processed while a bin that only has a single image may not be processed. In one example, producing the 3D image for a bin or interval includes performing a separate gridding reconstruction for the 3D images associated with the interval. The separate gridding reconstruction may use non-uniform Fast Fourier Transforms (NUFFT) with table based interpolation.

Once the per-bin images have been made, method 400 may continue, at 480, by registering the per bin images to a reference image. The registering may involve performing non-linear registration to register the 3D image for an interval to a 3D reference image associated with a reference interval in the set of position-dependent intervals. Thus, a per-bin image may be registered to an image associated with a reference bin to facilitate motion correcting for the motion described by the motion time course. In one example, registering an image includes applying a non-linear registration parameter associated with the non-linear registration to warp the 3D image for the interval to the reference image.

Once the registration has been performed, method 400 may continue, at 490, by producing a combined 3D image from 3D images associated with two or more different intervals. The combined 3D image may have a fourth resolution that is the same or different than the other resolutions.

In one embodiment, the third resolution or the fourth resolution may be selected after the set of 3D projections has been collected, after the set of first 3D images has been reconstructed, or after the set of second 3D images has been reconstructed. The resolutions may be selected to balance tradeoffs between temporal resolution and SNR/image quality. The tradeoffs are apparent in FIGS. 13A-13D, which show images reconstructed using 4 second, 8 second, 16 second, and 32 second temporal footprints respectively. Images with one temporal footprint may be produced to yield an image quality sufficient for presentation to radiologists for traditional image interpretation. Images with a different temporal footprint may be produced for use in quantitative analysis for the same data where increased image artifacts may be tolerated in return for greater temporal fidelity in the data. For example, high temporal resolution images can be used for quantitative time course analysis while broader temporal footprint images could be used for traditional radiologist interpretation.

To improve temporal resolution, the MRI apparatus may be controlled to acquire the set of 3D projections using non-Cartesian under-sampling. Since certain functional analyses may only be performed with clinically relevant precision if there is adequate temporal resolution, in one example, the MRI apparatus may be controlled to acquire the series of 3D data sets with a temporal resolution of better than 4 seconds per frame. Since certain functional analyses may only be performed with clinically relevant precision if there is adequate spatial resolution, example apparatus and methods improve temporal resolution without sacrificing spatial resolution. Therefore, method 400 may include controlling the MRI apparatus to acquire the series of 3D data sets with a spatial resolution of better than 1.8 mm$^3$.

Figure 5:
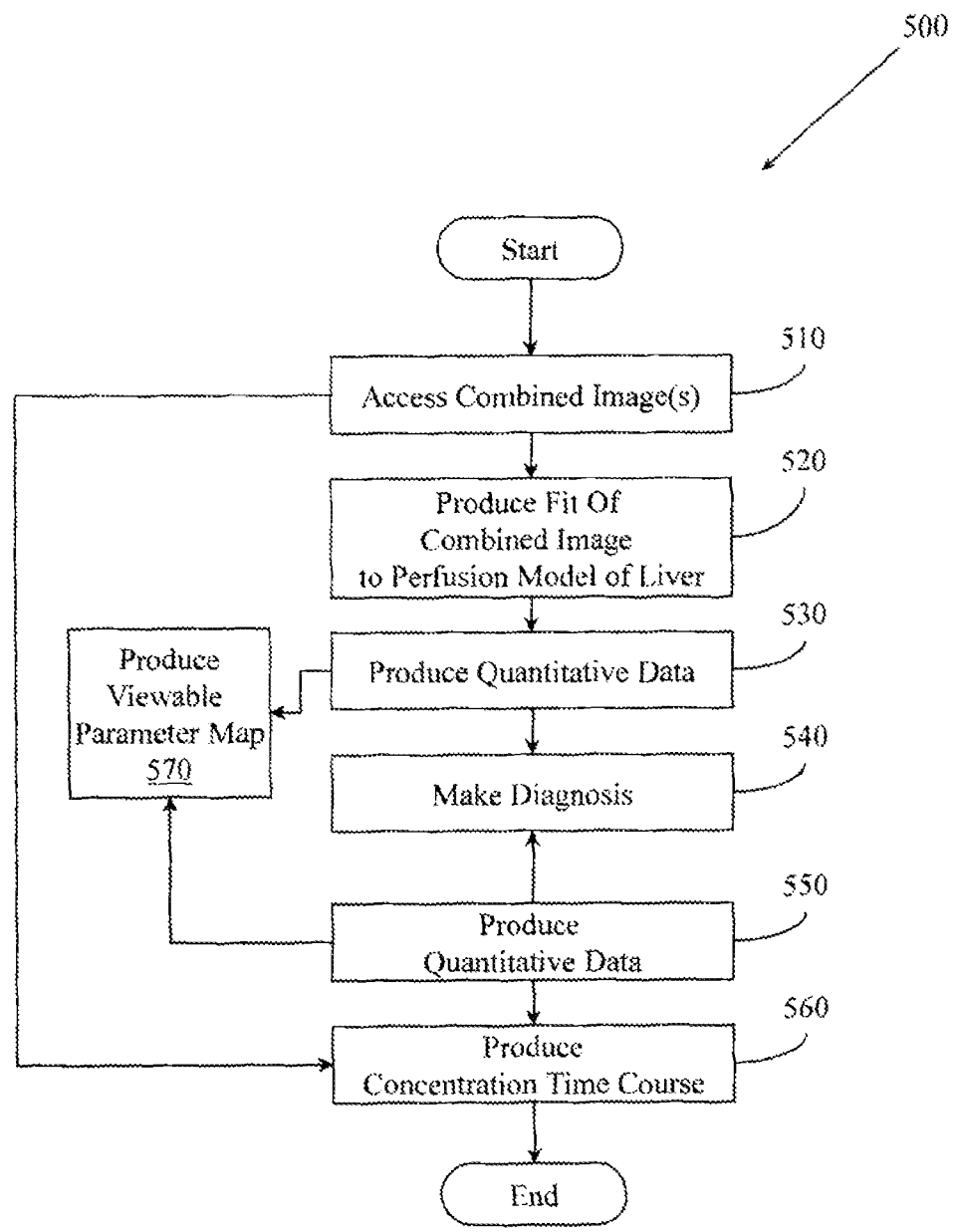
FIG. 5 illustrates an example method associated with an MRI 3D multi-echo non-Cartesian approach with self-navigation and self-registration.

FIG. 5 illustrates an example method 500 associated with using data produced from MRI using a 3D multi-echo non-Cartesian approach with self-navigation and self-registration. Method 500 may begin at 510 by accessing a 3D combined image. Method 500 may then proceed, at 520, to produce a fit of the combined 3D image to a model of the liver. In one embodiment, the model may be a dual-input single compartment perfusion model of the liver. Other models may be employed.

Once the fit has been produced, method 500 may continue, at 530, by producing quantitative data about the liver. The quantitative data may be based, at least in part, on the fit of the combined 3D image and on signal intensities in the combined 3D image. The signal intensities may be compared to known reference signal intensities acquired from reference samples. For example, phantoms may be placed in the bore with the patient and signal intensities from the phantoms can be compared to the signal intensities in the combined image.

The quantitative data may concern, for example, perfusion, total hepatic perfusion, arterial fraction, distribution volume, distribution time, mean transit time, arterial perfusion, portal venous perfusion, vascular transit time, fractional vascular volume, or fractional extravascular extracellular volume. In one embodiment, the quantitative data may be analyzed at 540 to produce a diagnosis of cirrhosis in the liver. Cirrhosis may be diagnosed when total liver perfusion is below 35/ml/min/100 ml, the portal perfusion is below 15/ml/min/100 ml, the arterial perfusion is above 20/ml/min/100 ml, the portal fraction volume is below 40 percent, or the mean transit time is above 30 seconds.

In one embodiment, method 500 may access a series of combined images at 510 and then proceed, at 560, by producing a 4D image or concentration time course from a series of combined 3D images. The fourth dimension is time. Once again, the 4D image may be analyzed to produce quantitative data about the liver. Producing the quantitative data may include converting signal time courses to contrast agent concentrations. The signal time courses may be associated with, for example, the celiac artery, the portal vein, the liver parenchyma, or other anatomy.

In one example, producing the quantified value for the hepatic perfusion parameter includes converting a signal intensity value in a member of the series of 3D data sets to a value describing the concentration of the contrast agent. Converting the signal intensity value may be based, at least in part, on a reference signal intensity value associated with a reference sample of the contrast agent. Thus, in one embodiment, method 500 may include acquiring the reference signal from the reference sample during the acquisition of at least one of the 3D data sets. The reference sample may provide, for example, a known concentration(s) of the contrast agent at a known location(s). For example, a vial(s) having compartments with four different known concentrations of contrast agent may be placed on the patient whose liver is being examined.

Method 500 may also include, at 570, producing and displaying a viewable parameter map of the quantitative data (e.g., hepatic perfusion parameter). In one embodiment, producing the viewable parameter map includes performing pixel-wise parameter mapping to produce a pixel-wise parameter map. In one embodiment, the pixel-wise parameter may be segmented by thresh-holding signal intensity values in a frame during enhancement.

While FIGS. 4 and 5 illustrate various actions occurring in serial, it is to be appreciated that various actions illustrated in FIGS. 4 and 5 could occur substantially in parallel.

By way of illustration, a first process could acquire nuclear magnetic resonance (NMR) signals, a second process could reconstruct the NMR signals, and a third process could produce quantified perfusion values. While three processes are described, it is to be appreciated that a greater and/or lesser number of processes could be employed and that lightweight processes, regular processes, threads, and other approaches could be employed.

In one example, a method may be implemented as computer executable instructions. Thus, in one example, a computer-readable storage medium may store computer executable instructions that if executed by a machine (e.g., processor) cause the machine to perform a method (e.g., methods 400 or 500). While executable instructions associated with the above methods are described as being stored on a computer-readable storage medium, it is to be appreciated that executable instructions associated with other example methods described herein may also be stored on a computer-readable storage medium.

Figure 6:
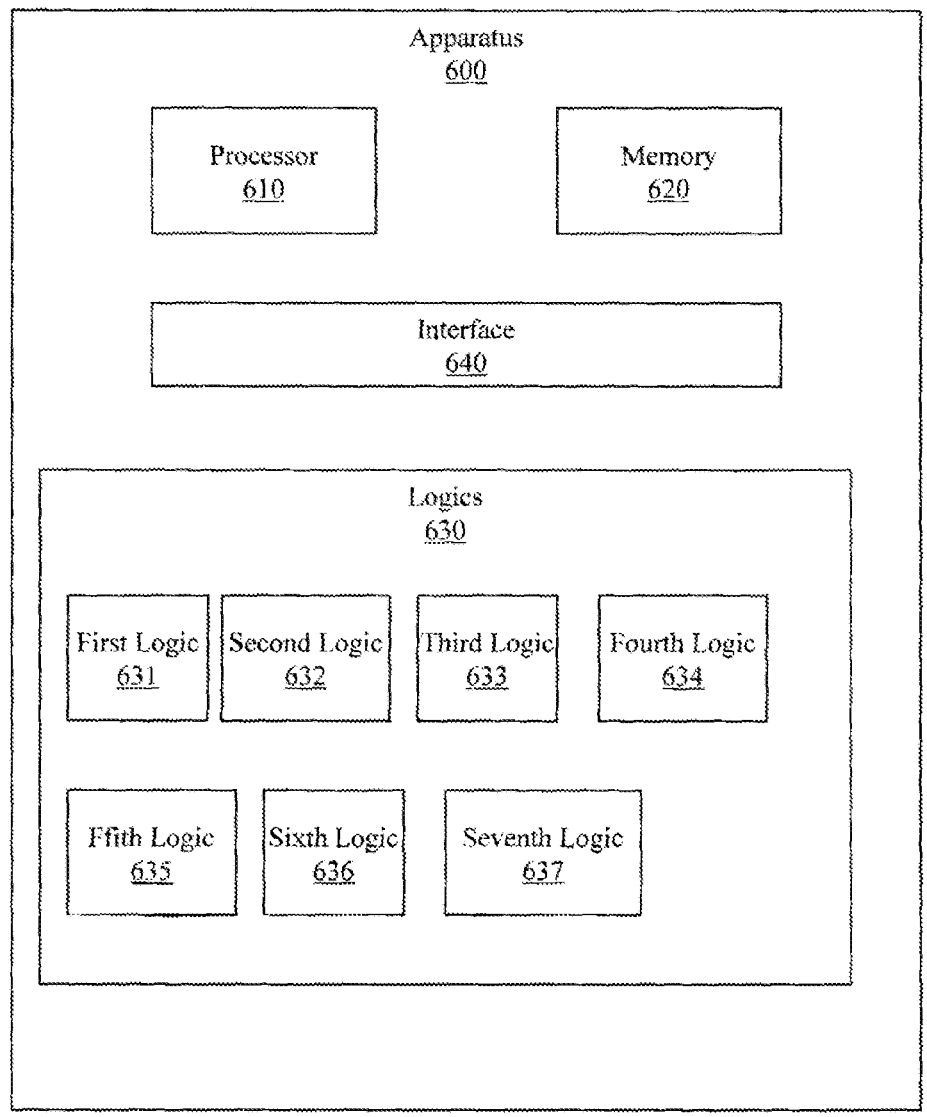
FIG. 6 illustrates an example apparatus associated with an MRI 3D multi-echo non-Cartesian approach with self-navigation and self-registration.

FIG. 6 illustrates an apparatus 600 for performing MRI-based quantitative liver perfusion analysis using a 3D multi-echo non-Cartesian EPI approach for acquiring data during a DCE MRI procedure. Apparatus 600 includes a processor 610, a memory 620, a set 630 of logics, and an interface 640 to connect the processor 610, the memory 620, and the set 630 of logics. In one embodiment, apparatus 600 may be a special purpose computer that is created as a result of programming a general purpose computer. In another embodiment, apparatus 600 may include special purpose circuits that are added to a general purpose computer to produce a special purpose computer.

In one embodiment, the set 630 of logics includes a first logic 631 that is configured to acquire 3D projections associated with NMR signals acquired from a liver experiencing NMR in response to a 3D multi-echo non-Cartesian EPI pulse sequence. The sequence may resemble the sequence described in Lee. In one embodiment, the first logic 631 is configured to produce a field map and a sensitivity map from the 3D projections. When the field map or sensitivity map are available, the first logic 631 may correct for susceptibility related distortions in the 3D projections based, at least in part, on the field map or sensitivity map.

In one embodiment, the first logic 631 may be configured to acquire the 3D projections by performing two or more pseudo-random rotations of a single 2D multi-echo non-Cartesian readout that produces a set of 2D projections. The two or more pseudo-random rotations populate 3D spherical k-space with the 2D projections by rotating a sampling pattern. The first logic 631 may also be configured to re-order the 3D projections.

Apparatus 600 may also include a second logic 632 that is configured to reconstruct the projections into a first set of images and a second set of images. The first set of images may have a first resolution of better than 2.0 mm and the second set of images may have a second resolution of less than 10.0 mm. Different resolutions may be employed. In one embodiment, the second logic 632 may be configured to reconstruct the projections using a compressed sensing with gradient descent with sparsification (GraDeS) approach. Other reconstructions may be employed.

Apparatus 600 may also include a third logic 633 that is configured to identify two or more position dependent bins into which members of the first set of images are to be binned. The intervals or bins may be selected based, at least in part, on a path described by navigator data in the second set of images. In one embodiment, the navigator data may include one or more voxels associated with the dome of the liver. The path described by the navigator data in the second set of images may identify two or more locations at which the liver is located during respiration. The two or more different locations may be produced by motion of the liver in the superior/inferior direction. In one embodiment, the third logic 633 may define a pencil-beam navigator through the dome of the liver on a low resolution series of volumes reconstructed at 0.5 s intervals from a 1.0 s data window.

Apparatus 600 may also include a fourth logic 634 that is configured to bin a member of the first set of images into one of the two or more position dependent bins. The member of the first set of images may be binned based, at least in part, on data in a corresponding member of the second set of images and the path described by the navigator data. Thus, motion parameters derived from the pencil beam navigator may be used to divide the acquired projections into a series of respiratory motion bins.

Apparatus 600 may also include a fifth logic 635 that is configured to combine images in a bin into a combined image for the bin. Thus, projections over a full scan that fall within a given bin are used to reconstruct time course average volumes for the different respiratory positions. In one embodiment, the fifth logic 635 may be configured to combine images in a bin by performing a separate gridding reconstruction for images in the bin using non-uniform Fast Fourier Transforms (NUFFT) with table based interpolation.

Apparatus 600 may also include a sixth logic 636 that is configured to register the combined bin image to a reference image associated with a reference bin. In one embodiment, the sixth logic 636 may be configured to register the combined bin image to a reference image by performing non-linear registration of the combined bin image to the reference image. In one embodiment, the non-linear registration may be performed using FMRT from FMRIB.

Apparatus 600 may also include a seventh logic 637 that is configured to integrate two or more combined bin images into a final combined image. The two or more combined images may, for example, be summed to produce a single image. The single image may then be displayed or analyzed quantitatively. In one embodiment, the resolution at which the final single image or the bin images are reconstructed may be chosen retrospectively based, at least in part, on whether the final single image is going to be displayed to a radiologist or analyzed quantitatively by an apparatus or process.

Figure 7:
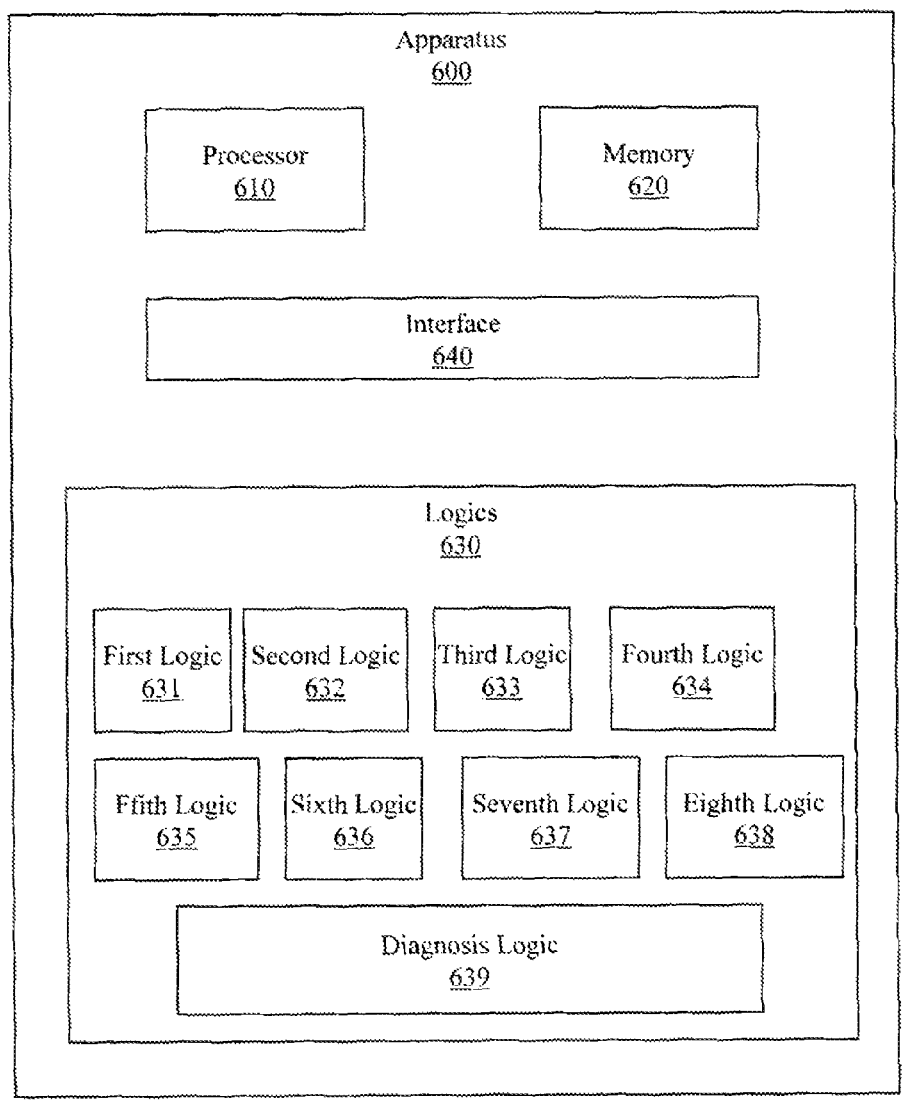
FIG. 7 illustrates an example apparatus associated with an MRI 3D multi-echo non-Cartesian approach with self-navigation and self-registration.

FIG. 7 illustrates another embodiment of apparatus 600. This embodiment of apparatus 600 includes an eighth logic 638 that is configured to produce a quantized value for a contrast agent concentration in the liver from a signal intensity in the final combined image. The quantized value may describe a perfusion parameter for the liver. The quantized value may describe, for example, total hepatic perfusion, mean transit time, arterial fraction, distribution time, arterial perfusion, portal venous perfusion, vascular transit time, fractional vascular volume, or fractional extravascular extracellular volume.

Apparatus 600 may also include a diagnosis logic 639 that is configured to produce a diagnosis of cirrhosis in the liver based, at least in part, on the quantized value. The diagnosis logic 639 may signal that the liver exhibits cirrhosis when total liver perfusion is below 35/ml/min/100 ml, when portal perfusion is below 15/ml/min/100 ml, when arterial perfusion is above 20/ml/min/100 ml, when portal fraction volume is below 40 percent, or when mean transit time is above 30 seconds. Other diagnosis may be made based on other values.

Figure 8:
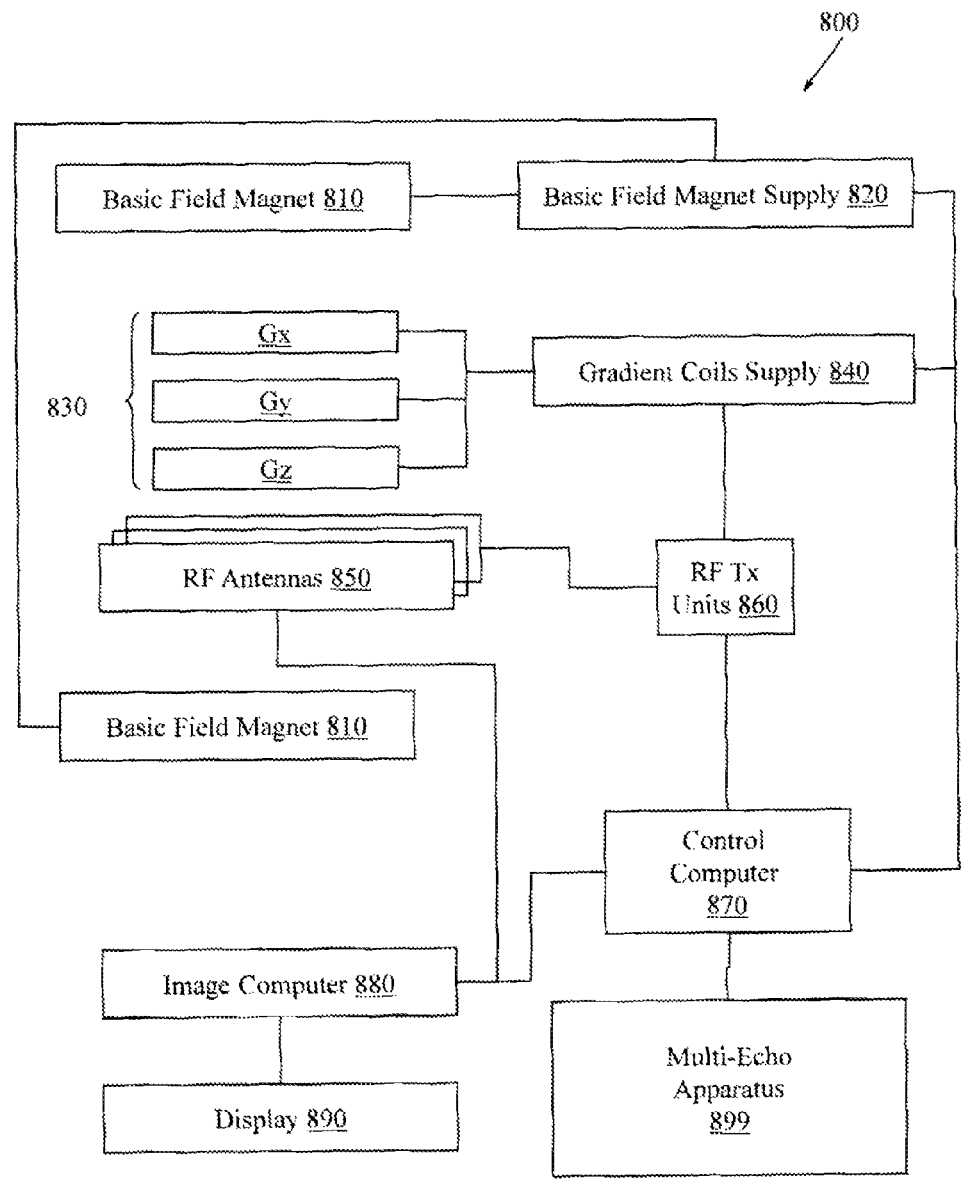
FIG. 8 illustrates an MRI apparatus configured to perform an MRI 3D multi-echo non-Cartesian approach with self-navigation and self-registration.

FIG. 8 illustrates an MRI apparatus 800. MRI apparatus 800 is configured with a multi-echo apparatus 899 to perform MRI-based quantitative liver perfusion analysis. The multi-echo apparatus 899 may be configured with elements of example apparatus described herein or may perform example methods described herein.

The apparatus 800 includes a basic field magnet(s) 810 and a basic field magnet supply 820. Ideally, the basic field magnets 810 would produce a uniform $B_0$ field. However, in practice, the $B_0$ field may not be uniform, and may vary over an object being imaged by the MRI apparatus 800. MRI apparatus 800 may include gradient coils 830 configured to emit gradient magnetic fields like $G_S$, $G_P$ and $G_R$ or Gx, Gy, and Gz. The gradient coils 830 may be controlled, at least in part, by a gradient coils supply 840. In some examples, the timing, strength, and orientation of the gradient magnetic fields may be controlled, and thus selectively adapted, during an MRI procedure.

MRI apparatus 800 may include a set of RF antennas 850 that are configured to generate RF pulses and to receive resulting NMR signals from an object to which the RF pulses are directed. In one embodiment, the RF antennas 850 are arranged as an array of parallel transmission coils that are individually controllable. How the pulses are generated and how the resulting MR signals are received may be controlled and thus may be selectively adapted during an MR procedure. Separate RF transmission and reception coils can be employed. The RF antennas 850 may be controlled, at least in part, by a set of RF transmission (Tx) units 860. An RF transmission unit 860 may provide a signal to an RF antenna 850. The RF transmission unit 860 may provide different signals to different RF antennas to produce different RF excitations from the different members of the array of parallel transmission coils. In one example, the different RF excitations may have different flip angles and different TRs. While early MRI sequences used RF pulses long enough to flip the longitudinal magnetization all the way to ninety degrees, later sequences may use smaller flip angles to increase acquisition speed.

The gradient coils supply 840 and the RF transmission units 860 may be controlled, at least in part, by a control computer 870. In one example, the control computer 870 may be programmed to control an NMR device as described herein. Conventionally, the magnetic resonance signals received from the RF antennas 850 can be employed to generate an image and thus may be subject to a transformation process like a two dimensional fast Fourier transform (FFT) that generates pixilated image data. The transformation can be performed by an image computer 880 or other similar processing device. The image data may then be shown on a display 890. While FIG. 8 illustrates an example MRI apparatus 800 that includes various components connected in various ways, it is to be appreciated that other MRI apparatus may include other components connected in other ways.

Some MRI applications desire both high resolution and high frame rates. Consider imaging a liver that is affected by motion associated with respiration or other motion. High resolution would facilitate improved diagnosis while high frame rates would facilitate improved motion artifact avoidance by acquiring an image while the liver is at rest. High frame rates also facilitate functional analyses that show the liver performing its functions and that show the changing concentration of a contrast agent in or near the liver. Motions other than respiration can also complicate liver and other imaging. Therefore improvement in frame rates that do not sacrifice resolution, and improvements in resolution that do not sacrifice frame rates, are constantly being sought. One way to improve frame rates is to increase the degree of under-sampling.

Acquiring an MR image may include acquiring both calibration data and image data. Acquiring adequate calibration data facilitates under-sampling image data and yet still achieving acceptable resolution. However, in some cases, acquiring fully-sampled calibration data sets may consume as much or more time than acquiring data for an MR image. Thus, applications like acquiring a full 3D multi-phase data set of the liver in a single breath hold may have been particularly challenging in conventional systems due, for example, to the time required to acquire fully-sampled data sets.

Conventionally, a single breath hold may only have allowed imaging a single volumetric image of the liver. When multiple views of the liver at different time points were required, multiple breath holds were required. Multiple breath holds may be challenging for patients that are having their liver imaged. Additionally, a patient may hold their breath differently on different breath hold attempts and thus images acquired during the different breath holds may be inconsistent. A further complication occurs as data is acquired further and further away from the time at which the calibration data was acquired. To mitigate these or other breath hold issues, example apparatus and methods facilitate performing liver MRI with a free breathing patient.

Logic 899 may provide means for acquiring nuclear magnetic resonance (NMR) signal data from a liver. In one embodiment, the NMR signal data is produced in response to a 3D multi-echo non-Cartesian pulse sequence applied during a free-breathing DCE procedure. Logic 899 may also provide means for producing a quantized value of a concentration of a contrast agent in the liver during the DCE procedure. The quantized value may be calculated from an image produced by combining a set of registered sub-volumes produced by image-domain self-navigation binning applied to the NMR signal data. Logic 899 may also provide means for displaying an image that includes a representation of the quantized value.

Figure 9:
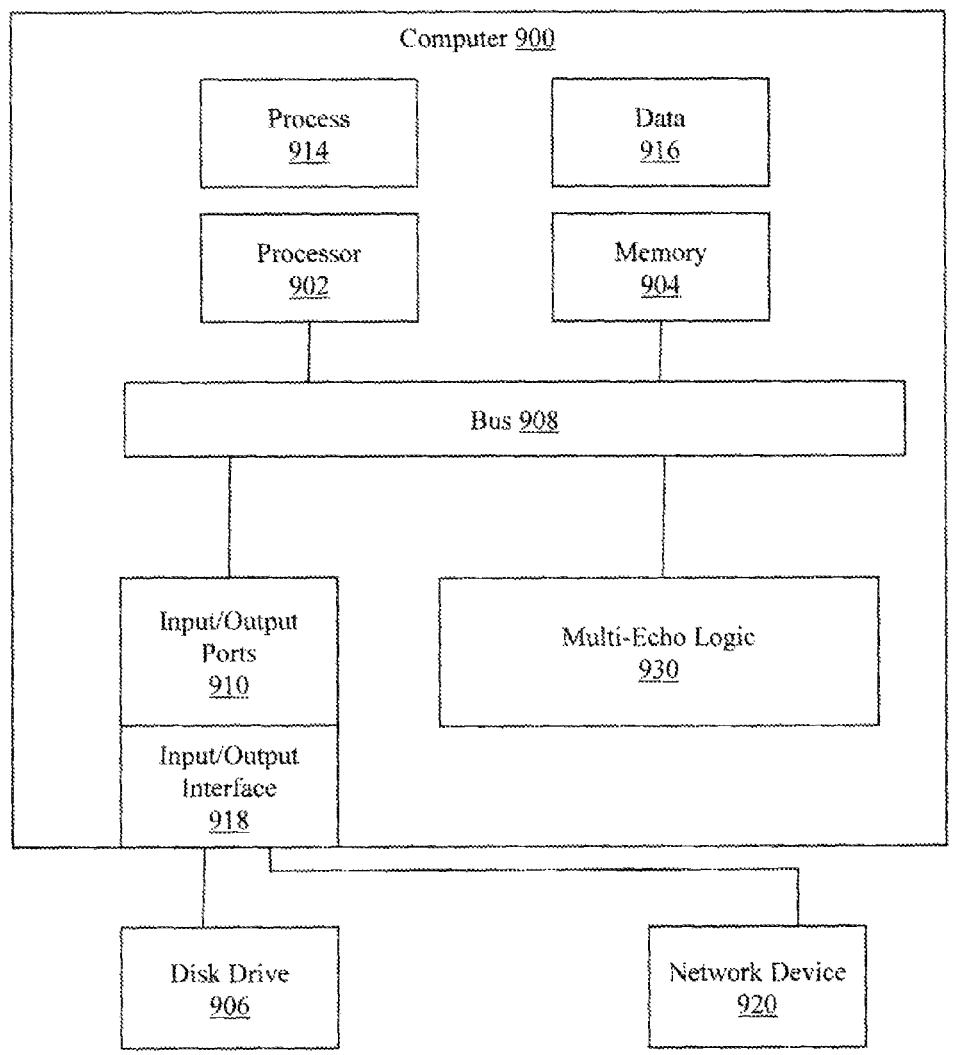
FIG. 9 illustrates a computer configured to perform an MRI 3D multi-echo non-Cartesian approach with self-navigation and self-registration.

FIG. 9 illustrates an example computing device in which example systems and methods described herein, and equivalents, may operate. The example computing device may be a computer 900 that includes a processor 902, a memory 904, and input/output ports 910 operably connected by a bus 908. In one example, the computer 900 may include a multi-echo logic 930 that facilitates performing MRI-based quantitative liver perfusion analysis using a 3D non-Cartesian multi-echo EPI approach in a DCE MRI. In different examples, the multi-echo logic 930 may be implemented in hardware, software, firmware, and/or combinations thereof. While the multi-echo logic 930 is illustrated as a hardware component attached to the bus 908, it is to be appreciated that in one example, the logic 930 could be implemented in the processor 902.

Thus, multi-echo logic 930 may provide means (e.g., hardware, software, firmware) for acquiring NMR signal data from the liver according to a 3D non-Cartesian multi-echo EPI approach associated with a DCE procedure. Multi-echo Logic 930 may also provide means (e.g., hardware, software, firmware) for producing a quantized value of the concentration of the contrast agent in the liver. In different embodiments the quantized value is accurate to within ten percent, twenty five percent, fifty percent, or a higher percent of the actual concentration of the contrast agent in the liver. Multi-echo logic 930 may also provide means for displaying an image that includes a representation of the quantized value. The means associated with multi-echo logic 930 may be implemented, for example, as an application specific integrated circuit (ASIC). The means may also be implemented as computer executable instructions that are presented to computer 900 as data 916 that are temporarily stored in memory 904 and then executed by processor 902.

Generally describing an example configuration of the computer 900, the processor 902 may be a variety of various processors including dual microprocessor and other multi-processor architectures. A memory 904 may include volatile memory and/or non-volatile memory. Non-volatile memory may include, for example, read only memory (ROM), and programmable ROM (PROM). Volatile memory may include, for example, random access memory (RAM), static RAM (SRAM), and dynamic RAM (DRAM).

A disk 906 may be operably connected to the computer 900 via, for example, an input/output interface (e.g., card, device) 918 and an input/output port 910. The disk 906 may be, for example, a magnetic disk drive, a solid state disk drive, a floppy disk drive, a tape drive, a solid state drive (SSD), a flash memory card, or a memory stick. Furthermore, the disk 906 may be a CD-ROM drive, a CD-R drive, a CD-RW drive, a DVD ROM drive, a Blu-Ray drive, or an HD-DVD drive. The memory 904 can store a process 914 and/or a data 916, for example. The disk 906 and/or the memory 904 can store an operating system that controls and allocates resources of the computer 900.

The bus 908 may be a single internal bus interconnect architecture and/or other bus or mesh architectures. While a single bus is illustrated, it is to be appreciated that the computer 900 may communicate with various devices, logics, and peripherals using other busses (e.g., PCIE, 1394, USB, Ethernet). The bus 908 can be types including, for example, a memory bus, a memory controller, a peripheral bus, an external bus, a crossbar switch, and/or a local bus.

The computer 900 may interact with input/output (i/o) devices via the i/o interfaces 918 and the i/o ports 910. I/O devices may be, for example, a keyboard, a microphone, a pointing and selection device, cameras, video cards, displays, the disk 906, or the network devices 920. The input/output ports 910 may include, for example, serial ports, parallel ports, and USB ports.

The computer 900 can operate in a network environment and thus may be connected to the network devices 920 via the i/o interfaces 918, and/or the i/o ports 910. Through the network devices 920, the computer 900 may interact with a network. Through the network, the computer 900 may be logically connected to remote computers. Networks with which the computer 900 may interact include, but are not limited to, a LAN, a WAN, and other networks.

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the embodiments described herein. Therefore, the invention is not limited to the specific details, the representative apparatus, and illustrative examples shown and described. Thus, this application is intended to embrace alterations, modifications, and variations that fall within the scope of the appended claims.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and other similar exemplary language indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer component", as used herein, refers to a computer-related entity (e.g., hardware, firmware, software in execution, combinations thereof). Computer components may include, for example, a process running on a processor, a processor, an object, an executable, a thread of execution, and a computer. A computer component(s) may reside within a process and/or thread. A computer component may be localized on one computer and/or may be distributed between multiple computers.

"Computer communication", as used herein, refers to a communication between computing devices (e.g., computer, personal digital assistant, cellular telephone) and can be, for example, a network transfer, a file transfer, an applet transfer, an email, an HTTP transfer, and other transfer. A computer communication can occur across, for example, a wireless system (e.g., IEEE 802.11), an Ethernet system (e.g., IEEE 802.3), a token ring system (e.g., IEEE 802.5), a LAN, a WAN, a point-to-point system, a circuit switching system, a packet switching system, and other system.

"Computer-readable storage medium", as used herein, refers to a medium that stores instructions or data. "Computer-readable storage medium" does not refer to propagated signals, per se. A computer-readable storage medium may take forms, including, but not limited to, non-volatile media, and volatile media. Non-volatile media may include, for example, optical disks, magnetic disks, tapes, flash memory, ROM, and other media. Volatile media may include, for example, semiconductor memories, dynamic memory (e.g., dynamic random access memory (DRAM), synchronous dynamic random access memory (SDRAM), double data rate synchronous dynamic random-access memory (DDR SDRAM), etc.), and other media. Common forms of a computer-readable storage medium may include, but are not limited to, a floppy disk, a flexible disk, a hard disk, a magnetic tape, other magnetic medium, a compact disk (CD), other optical medium, a random access memory (RAM), a read only memory (ROM), a memory chip or card, a memory stick, and other media from which a computer, a processor or other electronic device can read.

"Data store", as used herein, refers to a physical and/or logical entity that can store data. A data store may be, for example, a database, a table, a file, a data structure (e.g. a list, a queue, a heap, a tree) a memory, a register, and other stores. In different examples, a data store may reside in one logical and/or physical entity and/or may be distributed between two or more logical and/or physical entities.

"Logic", as used herein, includes but is not limited to hardware, firmware, software in execution on a machine, and/or combinations of each to perform a function(s) or an action(s), and/or to cause a function or action from another logic, method, and/or system. Logic may include a software controlled microprocessor, a discrete logic (e.g., ASIC), an analog circuit, a digital circuit, a programmed logic device, a memory device containing instructions, and other entities. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

An "operable connection", or a connection by which entities are "operably connected", is one in which signals, physical communications, and/or logical communications may be sent and/or received. An operable connection may include a physical interface, an electrical interface, and/or a data interface. An operable connection may include differing combinations of interfaces and/or connections sufficient to allow operable control. For example, two entities can be operably connected to communicate signals to each other directly or through one or more intermediate entities (e.g., processor, operating system, logic, software). Logical and/or physical communication channels can be used to create an operable connection.

"Signal", as used herein, includes but is not limited to, electrical signals, optical signals, analog signals, digital signals, data, computer instructions, processor instructions, messages, a bit, a bit stream, and other items, that can be received, transmitted and/or detected.

"Software", as used herein, includes but is not limited to, one or more executable instructions that cause a computer, processor, or other electronic device to perform functions, actions and/or behave in a desired manner. "Software" does not refer to stored instructions being claimed as stored instructions per se (e.g., a program listing). The instructions may be embodied in various forms including routines, algorithms, modules, methods, threads, and/or programs including separate applications or code from dynamically linked libraries.

"User", as used herein, includes but is not limited to one or more persons, software, logics, computers or other devices, or combinations of these.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, ABC, AAA, AAB, AABB, AABBC, AABBCC, (e.g., the data store may store only A, only B, only C, A&B, A&C, B&C, A&B&C, A&A&A, A&A&B, A&A&B&B, A&A&B&B&C, A&A&B&B&C&C). It is not intended to require one of A, one of B, and one of C. When the applicants intend to indicate "at least one of A, at least one of B, and at least one of C", then the phrasing "at least one of A, at least one of B, and at least one of C" will be employed.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

What is claimed is:

1. A method, comprising:
controlling a magnetic resonance imaging (MRI) apparatus to acquire a set of three dimensional (3D) projections from a liver that moves in a superior/inferior direction due to respiration, where the set of 3D projections are acquired using a 3D multi-echo non-Cartesian acquisition;
controlling the MRI apparatus to reconstruct members of the set of 3D projections in the superior/inferior direction into a corresponding set of first 3D images using a compressed sensing reconstruction, where members of the set of first 3D images have a first resolution;
controlling the MRI apparatus to reconstruct members of the set of 3D projections in plane into a corresponding set of second 3D images using a compressed sensing reconstruction, where members of the set of second 3D images have a second resolution that is less than the first resolution;
identifying one or more in-plane navigator voxels in members of the set of second 3D images;
producing a plot of the signal intensity of the one or more in-plane navigator voxels in two or more of the set of second 3D images as a function of time;
identifying a motion time course for the liver based, at least in part, on the plot of the signal intensity;
partitioning the motion time course into a set of position-dependent intervals;
associating a member of the set of first 3D images with a member of the set of position-dependent intervals based, at least in part, on the motion time course and the one or more in-plane navigator voxels;
producing a 3D image for an interval from the set of position-dependent intervals using members of the set of first 3D images associated with the interval, where the 3D image for the interval has a third resolution;
using non-linear registration to register the 3D image for the interval to a 3D reference image associated with a reference interval in the set of position-dependent intervals; and
producing a combined 3D image from 3D images associated with two or more different intervals, where the combined 3D image has a fourth resolution.

2. The method of claim 1, comprising ordering the set of 3D projections so that members of the set are equidistant to within a tolerance, where acquiring a member of the set of 3D projections includes performing two or more pseudo-random rotations of a single 2D multi-echo non-Cartesian readout, where the two or more pseudo-random rotations populate 3D spherical k-space by rotating a sampling pattern.

3. The method of claim 1, where the 3D multi-echo non-Cartesian acquisition is a radial echo planar imaging (EPI) acquisition.

4. The method of claim 1, where the 3D multi-echo non-Cartesian acquisition uses a fast low angle shot (FLASH) pulse sequence.

5. The method of claim 1, where the set of 3D projections are acquired during a free-breathing dynamic contrast enhanced (DCE) MRI procedure and where the one or more in-plane navigator voxels are located in the dome of the liver.

6. The method of claim 1, where the compressed sensing reconstruction uses a gradient descent with sparsification (GraDeS) approach and where the first resolution is at least 2.0 mm in the superior/inferior direction.

7. The method of claim 1, where the compressed sensing reconstruction uses a gradient descent with sparsification (GraDeS) approach and where the second resolution is at least 11 mm in the in-plane direction.

8. The method of claim 1, comprising producing a fit of the combined 3D image to a dual-input single compartment perfusion model of the liver.

9. The method of claim 8, comprising producing quantitative data about the liver based, at least in part, on the fit of the combined 3D image and on signal intensities in the combined 3D image.

10. The method of claim 9, where the quantitative data concerns one or more of, perfusion, total hepatic perfusion, arterial fraction, distribution volume, distribution time, mean transit time, arterial perfusion, portal venous perfusion, vascular transit time, fractional vascular volume, or fractional extravascular extracellular volume.

11. The method of claim 10, comprising producing a diagnosis of cirrhosis in the liver based, at least in part, on the quantitative data, where the diagnosis of cirrhosis is made when:
total liver perfusion is below 35/ml/min/100 ml,
portal perfusion is below 15/ml/min/100 ml,
arterial perfusion is above 20/ml/min/100 ml,
portal fraction volume is below 40 percent, or
mean transit time is above 30 seconds.

12. The method of claim 1, comprising producing a 4D image from a series of combined 3D images.

13. The method of claim 12, comprising producing quantitative data about the liver based, at least in part, on a series of 4D images by converting signal time courses observed in the series of 4D images to contrast agent concentrations.

14. The method of claim 13, where the quantitative data concerns one or more of, perfusion, total hepatic perfusion, arterial fraction, distribution volume, distribution time, mean transit time, arterial perfusion, portal venous perfusion, vascular transit time, fractional vascular volume, or fractional extravascular extracellular volume.

15. The method of claim 14, comprising producing a diagnosis of cirrhosis in the liver based, at least in part, on the quantitative data, where the diagnosis of cirrhosis is made when:
total liver perfusion is below 35/ml/min/100 ml,
portal perfusion is below 15/ml/min/100 ml,
arterial perfusion is above 20/ml/min/100 ml,
portal fraction volume is below 40 percent, or
mean transit time is above 30 seconds.

16. The method of claim 1, where producing the 3D image for the interval includes performing a separate gridding reconstruction for the first 3D images associated with the interval using non-uniform Fast Fourier Transforms (NUFFT) with table based interpolation.

17. The method of claim 16, where producing the combined 3D image includes:
producing a registered image by applying a non-linear registration parameter associated with the non-linear registration to warp the 3D image for the interval to the reference image; and
combining the registered image with the reference image.

18. The method of claim 1, comprising creating a field map and a sensitivity map from the set of 3D projections and correcting for susceptibility related distortions in the set of 3D projections using the field map or sensitivity map.

19. The method of claim 1, where the third resolution or the fourth resolution are selected after the set of 3D projections has been collected, after the set of first 3D images has been reconstructed, or after the set of second 3D images has been reconstructed.

* * * * *